United States Patent [19]

Uemura et al.

[11] Patent Number: 4,690,822
[45] Date of Patent: Sep. 1, 1987

[54] NOVEL DRUG CARRIER AND PHARMACEUTICAL PREPARATION COMPRISING THE SAME

[75] Inventors: Toshinobu Uemura, Kishiwada; Toshiaki Okhuma, Osaka; Kiyohide Shinooka, Nishinomiya; Hiroshi Ishikuro, Ikeda; Yoshio Ueda, Koube, all of Japan

[73] Assignee: Fujisawa Pharmaceutical Co., Ltd., Osaka, Japan

[21] Appl. No.: 839,077

[22] Filed: Mar. 12, 1986

[30] Foreign Application Priority Data

Mar. 26, 1985 [GB] United Kingdom ................ 8507779

[51] Int. Cl.$^4$ .......................... A61K 9/66; A61K 9/52; A61K 9/48
[52] U.S. Cl. ..................................... 424/455; 424/458; 424/489
[58] Field of Search ...................... 424/19, 22, 36, 38; 514/455, 458, 489

[56] References Cited

U.S. PATENT DOCUMENTS

| | | | |
|---|---|---|---|
| 2,149,005 | 2/1939 | Bockmuhl et al. | 424/14 |
| 2,805,977 | 9/1957 | Robinson et al. | 424/38 |
| 2,875,130 | 2/1959 | Grass et al. | 424/38 |
| 3,108,046 | 10/1963 | Harbit | 424/38 |
| 3,126,321 | 3/1964 | Kurtz | 424/37 |
| 3,147,187 | 9/1964 | Playfair | 424/38 |
| 3,374,146 | 3/1968 | Blicharz et al. | 424/38 |
| 3,539,465 | 11/1970 | Hiestand et al. | 424/37 |
| 3,549,555 | 12/1970 | Hiestand et al. | 424/37 |
| 3,851,051 | 11/1974 | Miskel et al. | 424/37 |
| 3,857,933 | 12/1974 | Ross et al. | 424/20 |
| 3,984,494 | 10/1976 | Harreus et al. | 424/22 |
| 4,137,300 | 1/1979 | Sheth et al. | 424/38 |
| 4,235,870 | 11/1980 | Leslie | 424/38 |
| 4,343,789 | 10/1982 | Kawata et al. | 424/19 |
| 4,404,183 | 9/1983 | Kawata et al. | 424/19 |
| 4,421,736 | 12/1983 | Walters | 424/38 |
| 4,438,847 | 11/1984 | Augart | 424/38 |

FOREIGN PATENT DOCUMENTS 2553026  10/1976  Fed. Rep. of Germany ........ 424/38

Primary Examiner—Shep K. Rose
Attorney, Agent, or Firm—Oblon, Fisher, Spivak, McClelland & Maier

[57] ABSTRACT

The invention relates to a pharmaceutical oral capsule preparation filled with a substantially anhydrous mixture which is in solid or semi-solid form comprising:

(a) a drug or a drug treated by a conventional manner, each of which is in solid form, and (b) a drug carrier which is a semi-solid mixture comprising a selected aqueous polymer and a selected liquid oil, the ratio of aqueous polymer to liquid oil by weight being 2:1 to 1:40.

6 Claims, No Drawings

NOVEL DRUG CARRIER AND PHARMACEUTICAL PREPARATION COMPRISING THE SAME

This invention relates to the novel drug carrier capable of controlling the gastrointestinal transit of the pharmaceutical preparation and capable of controlling the release rate of drug from the dosage form, and to dosage forms comprising the same.

More particularly, it relates to drug carrier, which comprises aqueous polymer and oil, capable of controlling the rate of transit of the pharmaceutical preparation in the gastrointestinal tract and capable of controlling the release of drug from the pharmaceutical preparation, and to the pharmaceutical preparations comprising the same.

The convenience of sustained release preparations which maintain the blood concentration of the drug at desired level over a prolonged period of time has been recognized, and as such sustained release preparations, slow-release matrix type tablet in which active ingredients are imbedded in insoluble matrix (e.g., paraffin wax and polymeric resin) and slow-release granules in which active ingredients are coated with the polymeric film for diffusion control of active ingredients have been well known in the pharmaceutical art.

In case of the application of abovementioned pharmaceutical preparations, however, we often encounter the unsatisfactory absorption of drug from the pharmaceutical preparation into the blood stream.

In particular, when these types of pharmaceutical preparations are applied to the drug having the relatively short absorption site of the gastrointestinal lumen, unsatisfactory absorption extensively occurs.

The main reason for such unsatisfactory absorption is that the passage of ordinary used sustained release preparations along the drug absorption site is relatively fast. (From the viewpoint of this fast passage, hereinafter we call oridinary used dosage form as old dosage form).

Recently, the technique for the estimation of the gastrointestinal transit rate of dosage form, i.e. technique of $\gamma$-scintigraphy, has been spreadly used.

S. S. Davis et al. (Int. J. Pharmaceutics, 21, 167–177 (1984)) obtained the data for the gastro-duodenal transit time and the small intestinal transit time of the matrix tablet and granules, respectively.

The gastro-duodenal transit time and the small intestinal transit time of the matrix tablet are 164 min. (S.E. 92 min.) and 188 min. (S.E. 23 min.), respectively. In case of granules, the former transit time is 79 min. (S.E. 20 min.) as half-time and the latter transit time is 227 min. (S.E. 82 min.) as half-time, respectively.

If the absorption site of drug exists among duodenum to ileum, we must design the slow-release preparation from which one-hundred percent of drug is released during about 360 min.

If it is not so, the unsatisfactory absorption will be occurred.

In order to overcome the unsatisfactory absorption of old dosage form, the attempts to extend retaining the dosage form for a prolonged period time in stomach were carried out by several investigators.

For example, Prabhakar R. Sheth et al, in U.S. Pat. No. 4,167,558 described the floating dosage form in stomach.

The principle of such a floating system is that the density of floating system is lower than that of gastric fluid.

Therefore, such a floating system owes to the existence of fluid in stomach.

Unfortunately, it is known that the passage of water administered in the fasting state through pylorus is relatively fast, i.e., A. Hurwitz (Gastroenterology, 71, 268–273 (1976)) obtained 13.1 min. (S.E. 0.7 min.) as half-time of the passage of fluid through pylorus.

Moreover, in he fasting state the interdigestive migrating contractions (IMC) occurs at periodic interval of about 100 minutes.

This IMC may let the floating system push out from the stomach. Consequently, the reliability of the floating system must be poor.

The inventors of the present invention have discovered drug carrier comprising the aqueous polymer and oil could control the gastrointestinal transit rate and the drug release, and could overcome the disadvantages of old dosage forms.

The present invention is explained in more detail in the following.

Suitable "aqueous polymer" to be used in drug carrier of the present invention may include polyethylene oxide, polyvinyl alcohol, polyvinyl pyrrolidone, cellulose derivatives (e.g., hydroxypropylmethylcellulose, methylcellulose, ethylcellulose, hydroxyethylcellulose, hydroxypropylcellulose, sodium carboxymethylcellulose, etc.), dextran, gelatin, pectin, sodium poly(acrylic acid), carboxypolymethylene (Carbopol®), poly-L-lysin, pullulan, sodium alginate, chitosan, gums (e.g., acacia, gum tragacanth, xanthan gum, guar gum, karaya gum, etc.) and the like.

Suitable "oil" to be used in drug carrier of the present invention may include fats and fatty oils such as vegetable fat and oil (e.g., arachis oil, cottonseed oil, sesame oil, etc.), animal oil and fat (e.g., lard, beef tallow, etc.), medium chain monoglyceride, medium chain diglyceride, medium chain triglyceride, etc.; hydrocarbon such as liquid paraffin, squalene, squalane, etc.; fatty acid such as oleic acid, linoleic acid, etc.; polyhydric alcohol such as ethylene glycol, propylene glycol, glycerin, etc.), etc.; and the like.

The ratio of aqueous polymer to oil by weight in our drug carrier can be suitably selected according to a kind of aqueous polymer and oil, degree of controlling the transit of the pharmaceutical preparation, etc., and the preferable ratio of aqueous polymer to oil by weight is 2:1 to 1:40 (more preferably 3:2 to 1:30, most preferably 1:1 to 1:20).

The ratio of drug to our drug carrier by weight in the pharmaceutical preparation can be suitably selected according to a kind of our drug carrier and drug, degree of controlling the transit of the pharmaceutical preparation, etc., and the preferable ratio of drug to our drug carrier by weight is 3:2 to 1:400 (more preferably 1:1 to 1:300, most preferably 1:3 to 1:200).

The present invention is explained according to the following Examples.

[DRUG IN EXAMPLES]

(1) 7-[2-(2-Aminothiazol-4-yl)-2-carboxymethoxyiminoacetamido]-3-vinyl-3-cephem-4-carboxylic acid (syn isomer) (hereinafter referred to as FK 027)
(2) Cephalexin (hereinafter referred to as CEX)

(3) Isopropyl 6-cyano-5-methoxycarbonyl-2-methyl-4-(3-nitrophenyl)-1,4-dihydropyridine-3-carboxylate (hereinafter referred to as FK 235)

(4) 3,4-Dihydro-6-(3,4-dimethoxyphenyl)-1-ethyl-3-methyl-4-(2,4,6-trimethylphenylimino)-2(1H)-pyrimidinone (hereinafter referred to as FR 58664).

EXAMPLE 1

The capsules in Table (1) were obtained by mixing poly(ethylene oxide) [average MW 5,000,000: prepared by Aldrich Chemical Company Inc., : hereinafter referred to as PEO], Miglyol 812 [Trademark: prepared by Dynamit Nobel Chemicals, hereinafter referred to as M812] and FK 027 and encapsulating them.

TABLE (1)

| Ingredients | Capsules (1) | (2) | (3) | (4) | (5) |
|---|---|---|---|---|---|
| FK 027 (mg potency) | 250 | 250 | 250 | 100 | 100 |
| PEO (mg) | 100 | 250 | 500 | 100 | 200 |
| M812 (ml) | 1 | 1 | 1 | 0.4 | 0.4 |

EXAMPLE 2

The capsules in Table (2) were obtained by mixing hydroxypropylmethylcellulose 2208 (15,000 cps) [Japan Pharmacopoeia, tenth edition; hereinafter referred to as HPMC], M812 and FK 027, and encapsulating them.

TABLE (2)

| Ingredients | Capsules (6) | (7) |
|---|---|---|
| FK 027 (mg potency) | 250 | 250 |
| HPMC (mg) | 50 | 250 |
| M812 (ml) | 1 | 1 |

EXAMPLE 3

CEX (160 mg) was suspended in 5% (W/V) hydroxypropylmethylcellulose 2910 (6 cps) (Japan Pharmacopoeia, tenth edition) i.e., aqueous TC-5R [Trademark: prepared by Shinetsu Chemical Co.] solution (700 ml) and the suspension was air-sprayed on "Non Pareil" (350–500 μm) (80 g) [Trademark: prepared by Freund Co.] by using "Flow Coater Mini" [Trademark: manufactured by Freund Co.] to give particles containing CEX.

The average diameter and CEX content of the obtained particles were 650 μm and 55.54% (W/W), respectively.

At the next step, the particles (70 g) obtained above were coated with the solution for enteric film, which was composed of hydroxypropylmethylcellulose phthalate "HP-50" (17.85 g) [Trademark: prepared by Shinetsu Chemical Co.], cetyl alcohol (3.15 g), ethanol (110 ml) and methylene chloride (110 ml), by using "Flow Coater Mini" to give enteric particles containing CEX hereinafter referred to as CEXep).

The average diameter and CEX content of CEXep were 750 μm and 43.22% (W/W), respectively.

The capsules in Table (3) were obtained by mixing CEXep, PEO and M812, and encapsulating them.

TABLE (3)

| Ingredients | Capsule (8) |
|---|---|
| CEXep (mg) | 578.4 |
| PEO (mg) | 500 |
| M812 (ml) | 1 |

To show the usefulness of drug carrier and the pharmaceutical preparations of this invention, the test results are explained as follows.

I.

Test (I)

Transit test

Test Samples

The test samples A to C in Table (4) were prepared by mixing FK 027, PEO, M812 and Indigocarmine (hereinafter referred to as IC), and ⅛ OZ capsule (prepared by Chemical & Pharmaceutical Company Inc.,) was used as capsule.

TABLE (4)

| Ingredients | Test samples A | B | C |
|---|---|---|---|
| FK 027 (mg potency) | 250 | 250 | 250 |
| PEO (mg) | 250 | 500 | 0 |
| M812 (ml) | 1 | 1 | 1 |
| IC (mg)* | 50 | 50 | 50 |

*: IC (blue dye) was included in order to visualize the test samples.

Test method

Each test sample together with water (40 ml) was orally administered to overnight fasting male beagle dogs (8–12 kg) and the dogs were left in the cage.

The dogs were anesthetized by an intravenous injection of sodium pentobarbital (30 mg/kg) at 3, 6 or 9 hours after administration and the inside of the stomach of each dog in left prone position was observed by the endoscope.

This test was carried out five times per each test sample.

Furthermore, the same test for non-disintegrating matrix tablet (10 mmφ×5 mm) instead of test samples was carried out two times as control experiments.

Test result

TABLE (5)

| Test samples | Time (hour) 3 | 6 | 9 |
|---|---|---|---|
| A | OOO OO | OXX XX | XXX XX |
| B | — | OOO XX | XXX XX |
| C | OXX XX | — | — |
| Non-disintegrating matrix tablet | XX | — | — |

O: Test sample (or tablet) remained in stomach.
X: Test sample (or tablet) did not remain in stomach.
—: Experiments were not carried out.

The test result shows that the gastro-duodenal transit times of the test samples A to C are significantly longer than that of non-disintegrating matrix tablet and the gastro-duodenal transmit time of the test samples depends on the concentration of PEO.

In the view point of endoscopic observation, our drug carrier visualized by IC was widely spread and adhered on the surface of stomach.

II.

Test (II)

Drug release test

Test samples

The test samples D to H in Tables (6) and (7) were prepared by mixing FK 027, PEO (or HPMC) and M812.

Test method

Dissolution test was carried out according to the method 2 in 10th edition of Japan Pharmacopoeia (paddle method, 100 rpm, 900 ml artificial gastric juice at 37° C.).

Test samples were poured into the dissolution vessel as ten droplets from a plastic syringe.

TABLE (6)

| Ingredients | Test samples | | |
|---|---|---|---|
| | D | E | F |
| FK 027 (mg potency) | 250 | 250 | 250 |
| PEO (mg) | 0 | 250 | 500 |
| M812 (ml) | 1 | 1 | 1 |

TABLE (7)

| Ingredients | Test samples | |
|---|---|---|
| | G | H |
| FK 027 (mg potency) | 250 | 250 |
| HPMC (mg) | 50 | 250 |
| M812 (ml) | 1 | 1 |

Test result

The dissolution profiles of test samples are given in the following table (8).

TABLE (8)

| Test samples | medium | Cumulative amount of released drug (%) | | | | | |
|---|---|---|---|---|---|---|---|
| | | 0.5 hr | 1 hr | 2 hr | 3 hr | 4 hr | 5 hr |
| D | 1st fluid | 64.8 | 80.2 | 98.0 | 100.9 | | |
| E | " | 11.4 | 27.3 | 51.9 | 68.6 | 83.1 | 91.6 |
| F | " | 7.9 | 14.6 | 27.2 | 41.8 | 54.3 | 65.4 |
| G | " | 47.6 | 60.9 | 79.4 | 93.8 | 99.9 | 100.0 |
| H | " | 38.6 | 50.5 | 61.8 | 68.3 | 73.4 | 78.1 |

These results indicate that the increase of the amount of aqueous polymer in drug carrier make retard the rate of drug release.

III.

Test (III)

Serum concentration test—(1)

(i) new dosage form (N.D.F.) of type 1
Preparation of test sample
The test samples I to O in Tables (9) and (10) were prepared by mixing FK 027, PEO (or HPMC) and M812.

The samples with 1 ml of M812, and 0.4 ml of M812 were encapsulated into ⅛ OZ capsule, and 1/70 OZ capsule respectively.

Hereinafter, we refer this type of new dosage form (N.D.F.) in which the drug is included as non-treated mere powder to as N.D.F. type 1.

TABLE (9)

| Ingredients | Test samples | | | | |
|---|---|---|---|---|---|
| | I | J | K | L | M |
| FK 027 (mg potency) | 250 | 250 | 250 | 100 | 100 |
| PEO (mg) | 0 | 250 | 500 | 100 | 200 |
| M812 (ml) | 1 | 1 | 1 | 0.4 | 0.4 |

TABLE (10)

| Ingredients | Test samples | |
|---|---|---|
| | N | O |
| FK 027 (mg potency) | 250 | 250 |
| HPMC (mg) | 50 | 250 |
| M812 (ml) | 1 | 1 |

(ii) old dosage form (O.D.F.) of FK 027
The tablets having three different release rates (contained 125 mg potency of FK 027) were prepared as the representative of O.D.F. according to the usual procedure.

Dissolution rates from O.D.F. of FK 027 were determined by the method described in 10th edition of Japan Pharmacopoeia (paddle method, 100 rpm, 900 ml artificial gastric juice at 37° C.).

The obtained data were shown in the following table (11).

TABLE (11)

| Test samples | cumulative amounts of released FK 027 (%) | | | | | |
|---|---|---|---|---|---|---|
| | 0.5 hr | 1 hr | 2 hr | 3 hr | 4 hr | 5 hr |
| fast-release O.D.F. (FK 027) | 10.9 | 26.4 | 56.7 | 78.2 | 91.5 | 95.7 |
| medium-release O.D.F. (FK 027) | 4.2 | 10.4 | 26.2 | 44.2 | 58.2 | 72.1 |
| slow-release O.D F. (FK 027) | 3.6 | 6.7 | 20.0 | 26.7 | 37.3 | 48.2 |

(iii) Determination of serum concentration of FK 027:
Each test sample was orally administered to six beagle dogs (male, 8–12 kg) which had been withheld from any food overnight. 20 ml of FK 027 Phosphate buffered solution (250 mg or 125 mg potency) was administered as control of each beagle dog.

Immediately after the administration of each sample, 40 ml of water (20 ml in case of control solution) was administered.

The assay for serum concentration of FK 027 was made by high performance liquid chromatographic method (HPLC method).

(iv) Test result
The results of FK 027 serum concentration from N.D.F. and O.D.F. were given in Tables (12) and (13).

It can be seen from the comparison of the results of N.D.F. with those of O.D.F. that N.D.F. in, particularly, the case of larger amounts of polymer gives the prolonged and higher level of serum concentration, namely, at least the peak concentration at 10 hours was obtained.

On the other hand, three O.D.F. give the decrease of serum concentration after the point of 6 hours.

TABLE (12)

| Test samples | Serum concentration of FK 027 of N.D.F. | | | | | | | | | | | | | | AUC (0-24 H) |
|---|---|---|---|---|---|---|---|---|---|---|---|---|---|---|---|
| | serum concentration (μg/ml) | | | | | | | | | | | | | | (μg · hr/ml) |
| | 0.5 hr | 1 hr | 2 hr | 4 hr | 6 hr | 8 hr | 10 hr | 11 hr | 12 hr | 14 hr | 16 hr | 18 hr | 20 hr | 24 hr | |
| I | 4.1 | 12.3 | 23.5 | 28.2 | 23.8 | 19.4 | 19.5 | — | — | — | — | — | — | 4.5 | 376.8 |
| control | 6.4 | 18.8 | 23.3 | 21.3 | 17.6 | 13.9 | — | 11.4 | — | — | — | — | — | 4.6 | 285.8 |
| J | 3.1 | 5.2 | 9.3 | 18.7 | 20.5 | 19.3 | 23.0 | — | 24.6 | 17.6 | 14.5 | 15.2 | 11.5 | 7.5 | 375.4 |
| control | 7.4 | 21.6 | 27.8 | 24.8 | 20.2 | 14.2 | — | 11.3 | — | — | — | — | — | 4.1 | 303.4 |
| K | 0.7 | 1.7 | 5.6 | 14.2 | 18.4 | 19.2 | 21.1 | — | 22.1 | 16.9 | 13.4 | 14.6 | 11.8 | 7.8 | 340.5 |
| control | 6.4 | 22.3 | 28.8 | 29.9 | 24.6 | 16.6 | — | 13.1 | — | — | — | — | — | 3.9 | 342.9 |
| L* | 0.4 | 1.5 | 5.5 | 13.2 | 12.5 | 10.8 | 10.5 | — | — | — | — | — | — | 3.2 | 189.0 |
| control | 3.4 | 9.7 | 12.9 | 11.3 | 9.1 | 5.8 | 4.5 | — | — | — | — | — | — | 1.5 | 127.2 |
| M* | 0.0 | 0.5 | 3.2 | 8.5 | 12.6 | 15.0 | 14.1 | — | — | — | — | — | — | 3.7 | 216.1 |
| control | 5.4 | 11.0 | 14.7 | 13.9 | 9.6 | 8.2 | 7.8 | — | — | — | — | — | — | 1.8 | 171.4 |
| N | 2.9 | 6.6 | 14.5 | 31.0 | 36.0 | 33.4 | 34.9 | — | — | — | — | — | — | 7.5 | 560.8 |
| control | 13.5 | 27.5 | 36.6 | 34.7 | 24.0 | 20.5 | 19.4 | — | — | — | — | — | — | 4.6 | 428.2 |
| O | 0.0 | 3.0 | 9.8 | 23.7 | 26.4 | 23.9 | 24.1 | — | — | — | — | — | — | 8.1 | 414.4 |
| control | 6.4 | 18.8 | 23.3 | 21.3 | 17.6 | 13.9 | 11.4 | — | — | — | — | — | — | 4.6 | 285.8 |

*100 mg potency of FK 027 is contained in one dose.

TABLE (13)

| Test samples | Serum concentration of FK 027 of O.D.F. | | | | | | | | | AUC (0-24 H) |
|---|---|---|---|---|---|---|---|---|---|---|
| | serum concentration of FK 027 (μg/ml) | | | | | | | | | (μg · hr/ml) |
| | 0.5 hr | 1 hr | 2 hr | 4 hr | 6 hr | 8 hr | 10 hr | 11 hr | 24 hr | |
| fast-release O.D.F. (FK 027) | 0.4 | 2.8 | 12.8 | 29.6 | 32.1 | 26.1 | 24.9 | — | 5.7 | 436.2 |
| control | 8.8 | 21.6 | 27.1 | 23.2 | 18.2 | 15.1 | — | 12.2 | 4.1 | 306.1 |
| medium-release O.D.F. (FK 207) | 0.0 | 1.4 | 7.5 | 25.0 | 24.6 | 20.9 | 18.0 | — | 3.1 | 319.0 |
| control | 10.5 | 25.1 | 33.0 | 28.6 | 22.2 | 16.1 | — | 12.6 | 3.6 | 339.6 |
| slow-release O.D.F. (FK 207) | 0.0 | 0.6 | 3.2 | 9.0 | 12.8 | 12.5 | 12.1 | — | 2.1 | 185.4 |
| control | 4.9 | 21.4 | 31.7 | 31.0 | 24.2 | 16.1 | — | 13.4 | 4.2 | 351.2 |

From these results, the advantage of N.D.F. to O.D.F. is indicated clearly, which derives from more prolonged retaining in stomach of N.D.F. than O.D.F.

The estimation of N.D.F. for the absorption profiles from each dosage form into blood stream was carried out by using well-known Wagner & Nelson's equation (J. Wagner and E. Nelson, J. Pharm. Sci., 52, 610 (1963)).

The obtained cumulative amounts into blood stream of each sample are given in Table (14).

The results show that the absorption rate into blood stream from N.D.F. can be controlled by the amounts of polymer suspended in drug carrier.

This controlling ability for absorption of N.D.F. is due to the controlling ability of drug release from drug carrier as described in Test (II) (Drug release test).

The duration of absorption from N.D.F. is estimated as about more than 10 hours.

On the other hand, the obtained values of O.D.F. show the limited duration of absorption of about 6 hours in all three cases. The reason of these limited duration is that O.D.F. fastly passages out the absorption site while the drug release from O.D.F. is still maintaining.

TABLE (14)

| | Cumulative absorbed amounts of FK 027 from various dosage form | | | | | | | | | | | | | | AUC |
|---|---|---|---|---|---|---|---|---|---|---|---|---|---|---|---|
| Test samples | cumulative absorbed amounts (μg/ml) | | | | | | | | | | | | | | (μg · hr/m) |
| | 0.5 hr | 1 hr | 2 hr | 4 hr | 6 hr | 8 hr | 10 hr | 12 hr | 14 hr | 16 hr | 18 hr | 20 hr | 24 hr | | (β**) (hr⁻¹) |
| I | 4.2 | 12.7 | 25.3 | 33.8 | 33.4 | 32.2 | 35.2 | — | — | — | — | — | 32.8 | | 376.8(0.075) |
| J | 3.2 | 5.4 | 10.2 | 22.1 | 27.5 | 29.8 | 37.3 | 43.3 | 40.1 | 39.8 | 43.2 | 41.9 | 41.3 | | 375.4(0.090) |
| K | 0.7 | 1.8 | 6.1 | 16.8 | 24.3 | 29.0 | 35.1 | 40.6 | 39.4 | 39.2 | 43.2 | 43.2 | 43.2 | | 340.5(0.104) |
| L* | 0.4 | 1.6 | 5.9 | 15.6 | 17.6 | 18.3 | 20.3 | — | — | — | — | — | 23.0 | | 189.0(0.105) |
| M* | 0.0 | 0.5 | 3.4 | 9.9 | 16.3 | 21.6 | 23.7 | — | — | — | — | — | 26.4 | | 216.1(0.105) |
| N | 3.0 | 6.9 | 16.0 | 37.2 | 49.2 | 53.9 | 62.6 | — | — | — | — | — | 66.1 | | 560.8(0.105) |
| O | 0.0 | 3.1 | 10.3 | 26.8 | 33.2 | 34.4 | 38.3 | — | — | — | — | — | 39.2 | | 414.4(0.075) |
| fast-release O.D.F. | 0.4 | 2.9 | 13.6 | 34.0 | 41.8 | 40.8 | 44.0 | — | — | — | — | — | 43.2 | | 436.2(0.086) |
| medium-release O.D.F. | 0.0 | 1.4 | 8.0 | 29.0 | 33.9 | 35.1 | 36.3 | — | — | — | — | — | 37.2 | | 319.0(0.107) |
| slow-release O.D.F. | 0.0 | 0.6 | 3.4 | 10.4 | 16.4 | 18.6 | 20.6 | — | — | — | — | — | 20.5 | | 185.4(0.099) |

*100 mg potency of FK 027 is contained in one dose.
**In this calculation, elimination constant (β) after oral administration of FK 027 solution was used.

IV

Test (IV)

Serum concentration test—(2)

The influence of food on serum concentration of N.D.F. and O.D.F.

Test sample of N.D.F.

Test sample K described in Test III was used as the representative of N.D.F.

Test sample of O.D.F.

Test sample slow-release O.D.F. (FK 027) described in Test III was used as the representative of O.D.F.

Method

Food (100 g) was provided for three dogs at 30 minutes before the administration of test sample. After the administration of each sample, water (40 ml) was administered immediately.

Result

The test results are given in Table (15).

TABLE (15)

| Test samples | serum concentration of FK 027 (μg/ml) | | | | | | | | AUC (0-24 hr) |
|---|---|---|---|---|---|---|---|---|---|
| | 0.5 hr | 1 hr | 2 hr | 4 hr | 6 hr | 8 hr | 10 hr | 24 hr | (μg · hr/ml) |
| N.D.F.: fasting | 0.0 | 0.2 | 1.8 | 9.3 | 15.0 | 18.1 | 22.1 | 5.9 | 305.8 |
| N.D.F.: after meal | 0.0 | 0.0 | 1.0 | 4.0 | 11.3 | 22.1 | 29.2 | 10.8 | 385.5 |
| O.D.F.: fasting | 0.3 | 1.8 | 4.5 | 11.5 | 10.6 | 8.4 | 7.4 | 1.8 | 141.1 |
| O.D.F.: after meal | 1.2 | 1.4 | 4.2 | 13.6 | 23.9 | 26.7 | 23.6 | 7.1 | 374.9 |

The results of O.D.F. show the large discrepancy between the serum concentration of FK 027 at fasting and that after meal over the point of 6 hours and also show the decrease of AUC.

This large discrepancy between at fasting and after meal may be due to the difference of overall gastrointestinal transit time of O.D.F. between them.

In case of N.D.F., the difference between them was apparently small as a whole, and the test results show the almost same AUC.

These results show that N.D.F. prepared with the drug carrier of the present invention is much less influenced by meal than O.D.F.

V

Test (V)

Serum concentration test—(3)

(i) N.D.F. of type 2

If the solubility of the subject drug in gastric juice is relatively high, the drug release rate from the above-mentioned N.D.F. type 1 will be relatively faster than the retaining of drug carrier in stomach. Accordingly, in this case, we might lose the use of the advantage of the drug carrier.

The following N.D.F. type 2 should be preferably applied in such a case. We describe N.D.F. type 2 using CEX as a pertinent drug.

Test sample P

Capsule (8) in Table (3) was used as Test sample P (⅛ OZ capsule was used).

(ii) O.D.F. of CEX

To compare N.D.F. type 2 with O.D.F., two O.D.F. of CEX were prepared. The preparation procedure of O.D.F. of CEX was carried out according to the usual one.

The release rates of CEX from the obtained O.D.F. are given in the Table (16).

The method for the dissolution test is the same as that of Test (III).

TABLE (16)

| Test samples | Cumulative amounts of released CEX (%) | | | | | | | |
|---|---|---|---|---|---|---|---|---|
| | 0.5 hr | 1 hr | 2 hr | 3 hr | 4 hr | 6 hr | 8 hr | 10 hr |
| fast-release O.D.F. (CEX) | 24.3 | 34.6 | 46.0 | 57.1 | 66.2 | 78.2 | 84.3 | 88.3 |
| slow-release O.D.F. (CEX) | 12.1 | 21.1 | 30.3 | 40.7 | 47.5 | 59.8 | 68.4 | 79.8 |

(iii) Determination of serum concentration of CEX

These samples [sample P, fast-release O.D.F. (CEX) and slow-release O.D.F. (CEX)] were administered to the same 6 overnight fasting beagle dogs.

The determination of CEX serum concentration was carried out by using HPLC method. The results are shown in Table (17).

The results of sample P show the prolonged absorption of CEX into blood stream.

Two O.D.F. of CEX, however, show the decrease of CEX serum concentration after the point of 4 hours, and also the decrease of AUC.

By Wagner & Nelson's analysis [Table (18)], the duration of absorption of sample P, fast-release O.D.F. (CEX) and slow-release O.D.F. (CEX) were obtained as >10 hr, ca. 6 hr and ca. 6 hr, respectively.

TABLE (17)

| Test samples | serum concentration of CEX (μg/ml) | | | | | | | | AUC (0-24hr) |
|---|---|---|---|---|---|---|---|---|---|
| | 0.5 hr | 1 hr | 2 hr | 4 hr | 6 hr | 8 hr | 10 hr | 24 hr | (μg · hr/ml) |
| P | 0.0 | 0.0 | 0.4 | 4.4 | 10.7 | 11.6 | 10.2 | 2.2 | 151.0 |
| fast-release O.D.F. (CEX) | 1.4 | 3.8 | 10.1 | 11.8 | 9.0 | 6.0 | 3.7 | 0.3 | 104.0 |
| slow-release O.D.F. (CEX) | 0.0 | 1.6 | 5.1 | 7.0 | 6.1 | 4.8 | 2.7 | 0.0 | 66.3 |

TABLE (18)

| Test samples | cumulative absorbed amounts (μg/ml) | | | | | | | | AUC |
|---|---|---|---|---|---|---|---|---|---|
| | 0.5 hr | 1 hr | 2 hr | 4 hr | 6 hr | 8 hr | 10 hr | 24 hr | (0-24 hr (β)) (hr$^{-1}$) |
| P | 0.0 | 0.0 | 0.5 | 5.8 | 16.5 | 23.7 | 28.6 | 45.4 | 151.0 (0.286) |
| fast-release O.D.F. (CEX) | 1.5 | 4.3 | 12.6 | 20.5 | 23.7 | 25.0 | 25.4 | 30.0 | 104.0 (0.286) |
| slow-release O.D.F. (CEX) | 0.0 | 1.7 | 6.2 | 11.5 | 14.4 | 16.2 | 16.2 | 19.0 | 66.5 (0.286) |

It is found that the N.D.F. type 2 is superior to O.D.F. from abovementioned results.

N.D.F. type 2 is, of cource, not restricted to the above described dosage form.

Not only enteric-coated drug particle but also film (e.g., ethylcellulose) coated slow-release particle can be preferably used.

EXAMPLE 4

FK 235 (8.5 g) and TC-5R (25.5 g) were dissolved in a 1:1 mixture (850 ml) of ethanol and methylene chloride.

Low substituted hydroxypropylcellulose "L-HPC$_{LH31}$" [Trademark: prepared by Shin-etsu Co.] (42.5 g) was added to the above solution and suspended. The suspension was air-sprayed on "Non Pareil" (350–500 μm) (51.4 g) by using "Flow Coater Mini" to give particles which were sieved to give particles passing through a 24-mesh (710 μm).

Further, the suspension of L-HPC$_{LH31}$ (40 g) in a 1:1 mixture (800 ml) of ethanol and methylene Chloride dissolving FK 235 (8 g) and TC-5R (24 g) was air-sprayed on the above-mentioned particles (80 g) in the same way mentioned above to give particles containing solid dispersion form of FK 235. The average diameter and FK 235 content of obtained particles were 700 μm and 8.6% (w/w), respectively.

At the next step, the particles (70 g) containing FK 235 solid dispersion obtained above were coated with the solution for enteric film, which was composed of "HP-50" (14.4 g), cetyl alcohol (1.6 g), ethanol (160 ml) and methylene Chloride (160 ml), by using "Flow Coater Mini" to give enteric particles. (hereinafter referred to as FK 235 ep).

The average diameter and FK 235 content of FK 235 ep were 750 μm and 7.2% (w/w), respectively.

The capsule in Table (19) was obtained by mixing FK 235ep, PEO and M812, and encapsulating them.

TABLE (19)

| Ingredients | Capsule (9) |
|---|---|
| FK 235 ep (mg) | 111.1 mg (FK 235, 8 mg potency) |
| PEO (mg) | 500 |
| M812 (ml) | 1 |

VI:

Test (VI)

Serum Concentration test—(4)

Test samples:
(i) N.D.F. of FK 235

In order to elucidate the application of our drug carrier to hardly soluble Drugs, we prepared N.D.F. type 2 using FK 235 of which solubility in water is less than 2 μg/ml, and tested.

Capsule (9) in Table (19) was used as Test Sample Q (⅛ OZ capsule was used).

(ii) O.D.F. of KF 235

The plain tablet of FK 235 solid dispersion form (FK 235, 4 mg potency) prepared according to the usual procedure, and the capsule containing 111.1 mg of FK 235ep (FK 235, 8 mg potency) were used as O.D.F., and hereinafter referred to as reference (1) and reference (2), respectively.

Determination of plasma concentration of FK 235

Each test sample containing 8 mg potency of FK 235 was orally administered to six overnight fasting beagle dogs (male, 8–12 kg).

Immediately after the administration of each sample, water (40 ml) was administered.

The assay for plasma concentration of FK 235 was made by using ECD gas chromatographic procedure.

The results are shown in Table (20).

TABLE (20)

| Test samples | Plasma Concentration of FK235 (ng/ml) | | | | | | | | | AUC (0-24) (ng · ml$^{-1}$ · hr) |
|---|---|---|---|---|---|---|---|---|---|---|
| | 0.5 H | 1 H | 2 H | 4 H | 6 H | 8 H | 10 H | 12 H | 24 H | |
| Reference (1)* | 46.8 | 86.3 | 86.7 | 38.7 | 22.3 | 12.5 | 6.6 | 4.0 | 0.8 | 411.5 |
| Reference (2) | 25.1 | 34.1 | 46.3 | 32.3 | 14.3 | 10.2 | 7.7 | 7.9 | 5.4 | 324.5 |
| Q | 5.1 | 2.1 | 5.8 | 16.8 | 22.9 | 39.8 | 23.6 | 12.0 | 1.7 | 312.9 |

*Two tablets (FK 235, 4 mg potency × 2) were administered simultaneously.

The results of sample Q show the prolonged absorption of FK 235 into blood stream.

On the other hand, References (1) and (2) show the decrease of FK 235 plasma concentration after the point of 2 hours.

The preparation of other insoluble drug, FR 58664 was prepared in accordance with the similar method as that of the sample Q in test VI and studied.

In the case of FR 58664 N.D.F., satisfactory results were obtained.

These results indicate that our drug carrier can be applied to hardly soluble Drugs as FK 235 and FR 58664.

What we claim is:

1. A pharmaceutical oral capsule preparation filled with a substantially anhydrous mixture which is in solid or semi-solid form comprising:
   (a) a drug or a drug treated by a conventional manner, each of which is in solid form, and
   (b) a drug carrier which is a semi-solid mixture comprising an aqueous polymer selected from the group consisting of polyethylene oxide, polyvinyl alcohol, polyvinyl pyrrolidone, hydroxypropylmethylcellulose, methylceullose, ethylcellulose, hydroxyethylcellulose, hydroxypropylcellulose, sodium carboxymethylcellulose, dextran, gelatin, pectin, sodium poly(acrylic acid), carboxypolymethylene, poly-L-lysin, pullulan, sodium alginate, chitosan, acacia, gum tragacanth, xanthan gum, guar gum and karaya gum, and liquid oil selected from the group consisting of arachis oil, cottonseed oil, sesame oil, medium chain monoglyceride, medium chain diglyceride, medium chain triglyceride, liquid paraffin, squalene, squalane, oleic acid, linoleic acid, ethylene glycol, propylene glycol and glycerin, the ratio of aqueous polymer to liquid oil by weight being 2:1 to 1:40.

2. The pharmaceutical oral capsule preparation of claim 1, wherein the aqueous polymer is polyethylene oxide or hydroxypropylmethylcellulose.

3. The pharmaceutical oral capsule preparation of claim 1, wherein the liquid oil is medium chain triglyceride.

4. The pharmaceutical oral capsule preparation of claim 1, wherein the aqueous polymer is polyethylene oxide or hydroxypropylmethylcellulose and the liquid oil is medium chain triglyceride.

5. The pharmaceutical oral capsule preparation of claim 1, wherein the drug treated by a conventional manner is an enteric particle containing drug.

6. A method of controlling the gastrointestinal transit rate of a pharmaceutical preparation which comprises orally administering to a subject the pharmaceutical preparation of claim 1.

* * * * *